(12) United States Patent
Zhou et al.

(10) Patent No.: US 10,485,916 B2
(45) Date of Patent: Nov. 26, 2019

(54) BIOARTIFICIAL LIVER DEVICE

(71) Applicant: WUHAN TOGO MEDITECH CO., LTD, Wuhan (CN)

(72) Inventors: Ping Zhou, Wuhan (CN); Lu Liu, Wuhan (CN)

(73) Assignee: WUHAN TOGO MEDITECH CO., LTD, Wuhan (CN)

( * ) Notice: Subject to any disclaimer, the term of this patent is extended or adjusted under 35 U.S.C. 154(b) by 162 days.

(21) Appl. No.: 15/857,564

(22) Filed: Dec. 28, 2017

(65) Prior Publication Data
US 2018/0117236 A1 May 3, 2018

Related U.S. Application Data

(63) Continuation-in-part of application No. PCT/CN2016/106025, filed on Nov. 16, 2016.

(30) Foreign Application Priority Data

Jul. 29, 2016 (CN) .......................... 2016 1 0611600

(51) Int. Cl.
*A61M 1/36* (2006.01)
*C12M 3/00* (2006.01)
(Continued)

(52) U.S. Cl.
CPC ........ *A61M 1/3635* (2014.02); *A61M 1/3489* (2014.02); *C12M 3/00* (2013.01);
(Continued)

(58) Field of Classification Search
CPC .............. A61M 1/3635; A61M 1/3489; A61M 1/1698; A61M 1/1664; A61M 1/1662;
(Continued)

(56) References Cited

U.S. PATENT DOCUMENTS

| 5,368,555 A * | 11/1994 | Sussman | A61M 1/3472 604/6.05 |
| 6,372,482 B1 * | 4/2002 | Mitrani | A61M 1/3472 210/601 |
| 2013/0131423 A1 * | 5/2013 | Wang | A61M 1/3621 600/1 |

FOREIGN PATENT DOCUMENTS

| CN | 1231212 | * | 4/1998 | ............ C12M 29/04 |
| CN | 101549179 | * | 4/2009 | .......... A61M 1/1625 |

(Continued)

OTHER PUBLICATIONS

ISR for PCT/CN2016/106022 A1 (English language version) (Year: 2017).*

Primary Examiner — Michael L Hobbs
(74) Attorney, Agent, or Firm — Matthias Scholl P.C.; Matthias Scholl

(57) ABSTRACT

A bioartificial liver device including a bioreaction chamber having a plurality of semi-permeable membranes and a plurality of filter spaces each confined by two adjacent semi-permeable membranes; a plurality of liver cell perfusion ports each communicating with one of the filter spaces for introducing the liver cells into the filter spaces, and a positive peristaltic pump. In the device, the semi-permeable membranes are disposed substantially horizontal with respect to the ground, and the positive peristaltic pump is adapted to drive the plasma flow from the bottom wall of the device to the top wall. The device of the invention improves the cell loading and the area for substance exchange between the blood and the liver cells.

13 Claims, 1 Drawing Sheet

(51) Int. Cl.
  *A61M 1/34* (2006.01)
  *C12M 3/06* (2006.01)
  *C12M 1/00* (2006.01)
  *C12M 1/02* (2006.01)
  *A61M 1/16* (2006.01)

(52) U.S. Cl.
  CPC ............ *C12M 27/16* (2013.01); *C12M 29/04* (2013.01); *C12M 29/10* (2013.01); *C12M 29/12* (2013.01); *C12M 41/18* (2013.01); *A61M 1/1698* (2013.01); *A61M 2202/0415* (2013.01); *A61M 2205/7545* (2013.01); *A61M 2205/7581* (2013.01); *A61M 2210/1071* (2013.01)

(58) Field of Classification Search
  CPC ........ A61M 1/1629; A61M 2210/1071; A61M 2205/36; A61M 2205/3368; A61M 2205/7545; A61M 2205/7581; A61M 2202/0415; A61M 2202/0413; C12M 29/04; C12M 29/10; C12M 29/12; C12M 27/16; C12M 23/34; C12M 21/08; C12M 41/18; C12M 3/00
  See application file for complete search history.

(56) References Cited

FOREIGN PATENT DOCUMENTS

| | | | | |
|---|---|---|---|---|
| CN | 102225222 | * | 2/2011 | |
| CN | 205356253 | * | 12/2015 | ................ A61J 1/05 |

* cited by examiner

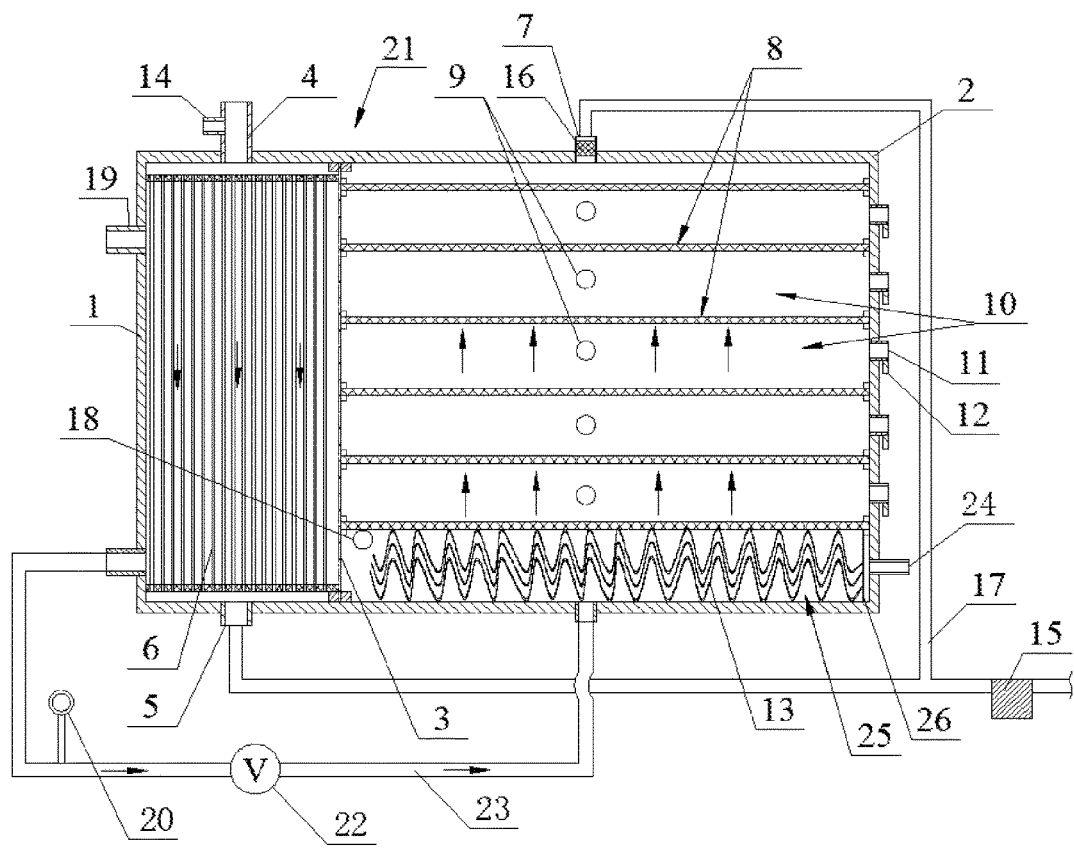

BIOARTIFICIAL LIVER DEVICE

CROSS-REFERENCE TO RELATED APPLICATIONS

This application is a continuation-in-part of International Patent Application No. PCT/CN2016/106025 with an international filing date of Nov. 16, 2016, designating the United States, now pending, and further claims foreign priority benefits to Chinese Patent Application No. 201610611600.0 filed Jul. 29, 2016. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The present disclosure relates to a bioartificial liver device.

Description of the Related Art

Liver transplantation is an effective treatment for liver failure. However, due to the problems including the shortage of donor organs, the expensive cost, and the potential risk of infection, liver transplantation cannot be applied in a large scale. In this context, artificial liver support systems are designed to replace the liver transplantation for the treatment of liver failure.

Artificial liver support systems include physical artificial liver devices and bioartificial liver devices. A physical artificial liver device has the defect of absorbing some beneficial proteins and coagulation factors and the like during treating the liver failure. A bioartificial liver device includes active liver cells (or other cells with liver function) which have liver functions such as detoxification, synthesis and biotransformation. Therefore, when using a bioartificial liver device for treating the liver failure, the patient's blood, can exchange substances with the cultured live cells. In this way, a bioartificial liver device has the detoxification and synthesis function of the liver.

A bioreactor is an essential part of a bioartificial liver device. An ideal bioreactor should meet the following requirements: (1) providing a suitable environment for the growing and the metabolism of liver cells; (2) having necessary liver functions; (3) having a small size; (4) having a minimum amount of dead space (i.e., useless space). Conventionally, the bioreactors of a bioartificial liver device are divided into the following four types: a hollow fiber tube type, a single layer/multilayer flat plate type, a perfusion bed/stent type, and a microcapsule suspension type. At present, the most widely used bioreactor is of a hollow fiber type. Nevertheless, the current bioreactors in a hollow fiber type have defects including a small capacity and a small cell load. In addition, in the current bioreactors in a hollow fiber type, the fiber filaments are easily clogged during the growing and the metabolism of liver cells.

SUMMARY OF THE INVENTION

In view of the above-described problems of existing bioartificial liver devices, such as a small capacity, and a small area for substance exchange between blood plasma and liver cells, one objective of the invention is to provide a bioartificial liver device which has a relatively large cell loading and treatment capacity, and is efficient, stable and uniform in substance exchange.

To achieve the above objectives, in accordance with one embodiment of the invention, there is provided a bioartificial liver device comprising: a housing comprising a top wall, a bottom wall, and a side wall; a chamber confined by the housing; a first semi-permeable membrane that is disposed within the chamber and divides the chamber into a plasma-separation chamber and a bioreaction chamber; a plurality of hollow fiber filaments disposed in the plasma-separation chamber; a blood inlet; a blood cell outlet; a first plasma opening; a second plasma opening; a separation pump; a plurality of second semi-permeable membranes disposed in the bioreaction chamber; a plurality of filter spaces; a plurality of liver cell perfusion port; a plasma outlet; and a positive peristaltic pump; in which the top wall and the bottom wall are adapted to be disposed substantially horizontal with respect to the ground; the top wall is adapted to be disposed above the bottom wall with respect to the ground; and the side wall connects the top wall with the bottom wall; the blood inlet is disposed on the top wall and communicates with the plasma-separation chamber, for the purpose of introducing blood of the patient into the plasma-separation chamber; the blood cell outlet is disposed on the bottom wall and communicates with the plasma-separation chamber; one end of each hollow fiber filament communicates with the blood inlet, and the other end of the each hollow fiber filament communicates with the blood cell outlet; the first plasma opening is disposed at the bottom of the side wall that is adjacent to the bottom wall and communicates with the plasma-separation chamber, for the purpose of outputting the plasma generated by the plasma-separation chamber from the plasma-separation chamber; the second plasma opening is disposed on the bottom wall and communicates with the bioreaction chamber, for the purpose of introducing the plasma generated by the plasma-separation chamber into the bioreaction chamber; the first and second plasma openings are connected with each other via the separation pump; the second semi-permeable membranes are disposed substantially parallel to each other and to the top wall or the bottom wall; each of the filter spaces is confined by two adjacent second semi-permeable membranes; each of the liver cell perfusion ports is disposed on the side wall and communicates with one of the filter spaces, for the purpose of introducing liver cells into the filter spaces; the plasma outlet is disposed on the top wall and communicates with the bioreaction chamber, for the purpose of outputting the plasma generated by the bioreaction chamber; the blood cell outlet and the plasma outlet are connected to the positive peristaltic pump; and the positive peristaltic pump is adapted to provide plasma generated by the bioartificial liver device into the body of the patient. In a class of one embodiments, the blood inlet comprises high-oxygen water inlet that introduces water having high oxygen content into the plasma-separation chamber for the purpose of oxygenating the plasma and supplying sufficient oxygen to the cultured cells.

In a class of one embodiment, a gas space is confined by the bottom wall and the one of the second semi-permeable membranes that is disposed adjacent to the bottom wall; a gas inlet that introduces air having oxygen is disposed on the side wall and communicates with the gas space; and a plurality of fiber filaments each of which breathes is disposed in the gas space and communicates with the gas inlet.

In a class of this embodiment, the second semi-permeable membranes and the first semi-permeable membrane are flat membranes and are fixedly connected to the housing.

In a class of this embodiment, the diameters of the pores among the second semi-permeable membranes are gradually decreased membrane by membrane, starting from the one of the second semi-permeable membranes that is adjacent to the bottom wall and ending to the one of the second semi-permeable membranes that is adjacent to the top wall.

The above preferred solution has the following beneficial effects. By setting the pore diameters of the second semi-permeable membranes to gradually decrease membrane by membrane from the bottom to the top of the bioreactor chamber, the second semi-permeable membranes effectively prevent clogging in the membranes and allows for generating a uniform plasma flow having a stable flow as well.

In a class of this embodiment, a third semi-permeable membrane is provided in the plasma outlet to prevent cells, cell products, or macromolecular substances in the bioreaction chamber that trigger allergy from entering into the body of the patient.

In a class of this embodiment, a sealed stent plate having a plurality of orifices is disposed in the gas space and between the gas inlet and the fiber filaments, and the sealed stent plate is disposed away from the gas inlet with a distance; each of the fiber filaments is clamped in one the orifices, and the fiber filaments communicate with the gas inlet via the sealed stent plate.

In a class of this embodiment, a plurality of pairs of a backup outlet and a pressure sensor is disposed on the side wall, each pair communicates with one of the filter spaces. The backup outlets of each two adjacent pairs are connected to each other through a valve.

The above pairs of the backup outlet and the pressure sensor provide the following beneficial effects. The pressure sensor detects whether there is a clogged second semi-permeable membrane between two adjacent filter spaces, and in the event of clogging, the two backup outlets of the two adjacent filter spaces are controlled to communicate with each other by adjusting the valve, so as to prevent circulation interruption caused by the clogged filter semi-permeable membrane by allowing the plasma to pass through the backup outlets among the two adjacent filter spaces to ensure the treatment going well.

In a class of this embodiment, the first and second plasma openings are connected to the separation pump via connection pipes; and one of the connection pipes is provided with a pressure detector.

In a class of this embodiment, a gas outlet or a reserved opening is disposed on the side wall and communicates with the gas space.

In a class of this embodiment, the bioartificial liver device further comprises a heat preserve jacket that functions to control the device at the temperature of 37° C., and a shaker that functions to shake the device; in which the heat preserve jacket covers the housing, and the shaker is arranged outside the housing and connected to the housing.

The above heat preserve jacket ensures the device in the temperature of 37° C. which is optimum for treatment, and the shaker assistants to avoid cell accumulation in the device.

In a class of this embodiment, a diameter of the pores on the first semi-permeable membrane is in the range of 0.3-5 micrometers, and a diameter of the pores on the one of the second semi-permeable membranes that is adjacent to the bottom wall is 5 micrometers.

Advantages of the bioartificial liver device according to embodiments of the present disclosure are summarized below. The second semi-permeable membranes that confine the filter spaces where the liver cells are contained and where the substance exchange between the liver cells and the blood is conducted, are disposed substantially to each other and to the top wall or the bottom wall of the housing that is adapted to be disposed substantially horizontal with respect to the ground. Furthermore, the second plasma opening that introduces the plasma separated from plasma-separation chamber into the bioreaction chamber is disposed below the plasma outlet for outputting the plasma generated by the bioreaction chamber with respect to the ground, and the plasma outlet is connected to the positive peristaltic pump so as to ensure the flow is conducted from the second plasma opening to the plasma outlet. The above structures ensure that the liver cells are uniformly disposed on the second semi-permeable membranes instead of accumulate in the bottom of the bioreaction chamber due to the gravity, and ensures that the substance exchange is conducted among all second semi-permeable membranes. This significantly increases cell load of the device, the area for substance exchange, and the utilization rate of the liver cells. In addition, the introduction of water having high oxygen content for oxygenating the plasma while ensuring oxygen supply to the cells as well as the fiber filaments that breathe and communicate with gas inlet for further providing sufficient oxygen, provides cells in an appropriate metabolic environment to protect cell activity improve cell culture effects, and facilitate maintenance of cell functions so at to improve the treatment effects. The plasma separated by the plasma-separation chamber is first introduced into the gas space disposed at the bottom of the bioreaction chamber, and then passes layer by layer through the second semi-permeable membranes that are spaced with an interval to make substance exchange with the liver cells within the filter space. In this way, the plasma can always maintain in a stable and uniform flow rate to better contact with the liver cells. Therefore, the exchange efficiency of the two substances is increased, and the effect of degrading plasma is improved. In addition, the second semi-permeable membranes and the third semi-permeable membrane serve to reduce the risk of liver cells entering human body along with the plasma. In addition, the temperature controlling and continuous shaking can facilitate providing a more suitable environment for the substance exchange so as to achieve an optimum treatment effect.

BRIEF DESCRIPTION OF THE DRAWINGS

The invention is described hereinbelow with reference to accompanying drawings, in which the sole FIGURE is a schematic diagram of a bioartificial liver device comprising semi-permeable membranes according to the present invention.

In the drawing, the following reference numbers are used: 1: plasma-separation chamber, 2: bioreaction chamber, 3: first semi-permeable membrane, 4: blood inlet, 5: blood cell outlet, 6: hollow fiber filament, 7: plasma outlet, 8: second semi-permeable membrane, 9: liver cell perfusion port, 10: filter space, 11: backup outlet, 12: pressure sensor, 13: fiber filament, 14: high-oxygen Water inlet, 15: positive peristaltic pump, 16: third semi-permeable membrane, 17: tubing, 18: gas outlet/reserved opening, 19: backup sample inlet of plasma separator, 20: pressure detector, 21: housing, 22: separation pump, 23: connection pipe, 24: gas inlet, 25: gas space, 26: sealed stent plate.

DETAILED DESCRIPTION OF THE EMBODIMENTS

To further illustrate the invention, experiments detailing a bioartificial liver device comprising semi-permeable membranes are described below. It should be noted that the following examples are intended to describe and not to limit the invention.

As shown in FIG. 1, a bioartificial liver device comprises: a housing comprising a top wall, a bottom wall, and a side wall; a chamber is confined by the housing 21. The chamber is subdivided into a plasma-separation chamber 1 and a bioreaction chamber 2 by a first semi-permeable membrane 3. The top wall and the bottom wall are adapted to be disposed substantially horizontal with respect to the ground; the top wall is adapted to be disposed above the bottom wall with respect to the ground; and the side wall connects the top wall with the bottom wall.

A blood inlet 4 is disposed on the top wall and communicates with the plasma-separation chamber 1, for the purpose of introducing blood of the patient into the plasma-separation chamber 1; a blood cell outlet 5 is disposed on the bottom wall and communicates with the plasma-separation chamber 1; and a plurality of hollow fiber filaments 6 is disposed in the plasma-separation chamber 1, one end of each hollow fiber filament 6 communicates with the blood inlet, and the other end of the each hollow fiber filament 6 communicates with the blood cell outlet; one end of the hollow fiber filaments 6 communicates with the blood inlet 4, and the other end of the hollow fiber filaments 6 communicates with the blood cell outlet 5.

A plasma outlet 7 is provided on the top wall of the housing 21. A plurality of second semi-permeable membranes 8 are substantially horizontally arranged with respect to the ground in the bioreaction chamber 2 for preventing free cells from passing through. Every two adjacent second semi-permeable membranes 8 and the side wall of the housing 21 confine an independent filter space 10. The side walls of the housing 21 corresponding to each independent filter space 10 is provided with a liver cell perfusion port 9. The bottom second semi-permeable membrane 8 that is adjacent to the bottom wall and the bottom wall of the housing 21 form a gas space 25. The gas space 25 is filled with fiber filaments 13 which are permeable to gas, and the side wall of the housing 21 corresponding to the gas space 25 is provided with a gas inlet 24 communicating with the fiber filaments 13. The plasma-separation chamber 1 and the bioreaction chamber 2 are connected via a separation pump 22. In particular, a first plasma opening that is disposed on the side wall of the housing 21 and communicates with the plasma-separation chamber 1 for outputting the plasma generated by the plasma-separation chamber 1, is connected to the separation pump 22 via a connection pipe 23, and a second plasma opening that is disposed on the bottom wall of the housing 21 and communicates with the bioreaction chamber 2 for introducing the plasma generated by the plasma-separation chamber 1 into the bioreaction chamber 2, is also connected to the separation pump 22 via a connection pipe 23. Both the second semi-permeable membrane 8 and the first semi-permeable membrane 3 are flat membrane, and are fixedly connected to the housing 21.

The diameters of the pores among the second semi-permeable membranes 8 gradually decrease membrane by membrane in the direction away from bottom wall to the top wall. By setting the surface pore diameters on the second semi-permeable membranes 8 to be decreased membrane by membrane, the second semi-permeable membranes 8 are prevented from clogging, and a uniform plasma flow having a stable rate is ensured as well.

A third semi-permeable membrane 16 is provided in the plasma outlet 7 for preventing cells from passing through the plasma outlet 7 into the body of the patient. The third semi-permeable membrane 16 serves to prevent cells, cell products, or macromolecular substance from entering the blood so as to prevent allergy.

The gas space 25 is further provided with a sealed stent plate 26 for preventing plasma/pre-filled liquid flowing in or out from the gas inlet 24. The sealed stent plate 26 is disposed at a distance away from the gas inlet 24, and comprises a plurality of orifices. One end of each gas permeable fiber filament 13 is clamped in one orifice, and the fiber filaments communicate with the gas inlet 24 through the space between the sealed stent plate 26 and the gas inlet 24.

The side wall of the housing 21 corresponding to the filter space 10 is further provided with a backup outlet 11 and a pressure sensor 12. The pressure sensor 12 detects whether there is a clogged second semi-permeable membrane 8 between two adjacent filter spaces 10. In the event of clogging, two backup outlets 11 communicating the two adjacent filter spaces 10 are connected by adjusting a valve (not shown) in order to prevent circulation interruption caused by the clogged filter semi-permeable membrane 8 by allowing the plasma to pass through the backup outlets 11, so that the treatment can be continued.

Further, a high-oxygen water inlet 14 is provided in and communicates with the blood inlet 4. And one of the connection pipes 23 is further provided with a pressure detector 20. Water having high oxygen content is introduced into the device through the high-oxygen water inlet 14 to oxygenate the plasma while ensuring the oxygen supply to the cells, thereby achieving a better cell culture effect.

The side wall of the housing 21 corresponding to the gas space 25 is provided with a gas outlet/reserved opening 18.

The device further comprises a heat preservation jacket (not shown) and a shaker (not shown) arranged outside the housing 21. The temperature of the heat preservation jacket maintains at 37° C. The bioartificial liver device of the invention has a temperature that is controlled to 37° C. by means of the heat preservation jacket and is continually shaken by means of the shaker to avoid cell accumulation thus achieving an optimum treatment effect.

The pore diameters of the first semi-permeable membrane 3 is 0.3 to 5 micrometers, and the pore diameter of the bottom second semi-permeable membrane 8 that is adjacent to the bottom wall is 5 micrometers.

The blood cell outlet 5 and the plasma outlet 7 are connected to a positive peristaltic pump 15 via by a tubing 17. Circulation in the system is driven by the positive peristaltic pump 15. The plasma-separation chamber 1 is also provided with a backup sample inlet 19.

The principle of the present invention is as follows:

Liver cell perfusion of the present invention is performed with a microcarrier perfusion method. That is, the cells adhered to the microcarriers are perfused through each liver cell perfusion port 9 along with the microcarriers, and the perfused volume is about two-thirds of the volume of the filter layer 10.

When blood enters the plasma separator 1 via the blood inlet 4, the blood is separated by means of the hollow fiber filaments 6. Blood cells and part of the plasma flow out of the blood cell outlet 5, and the remaining plasma enters the bioreactor 2 through the connection pipe 23. The plasma is first in the interlayer 25 with the fiber filaments 13. Oxygen is introduced into the interlayer 25 through the gas inlet 24. Then the plasma passes through the bottom second semi-permeable membrane 8 into the filter space 10, makes adequate reaction with the cells in the layer space 10, and enters the next filter space 10 after the reaction. In this manner, the plasma passes sequentially through the second semi-permeable membranes 8 layer by layer until it passes through the bottom second semi-permeable membrane 8. Finally, the plasma is discharged through the plasma outlet 7 and is mixed with the blood cells and the part of plasma discharged through the blood cell outlet 5 to be infused into the body.

The inventor has found that the horizontal arrangement of the second semi-permeable membranes 8 has the following advantages:

1. Plasma flows from the bottom to the top to resist some gravity effect to make the cell distribution more uniform. However, if the second semi-permeable membranes in the bioreactor are vertically arranged, the cells tend to be deposited at the bottom.

2. When the cells are deposited, the horizontally distributed cells are deposited on the second semi-permeable membranes 8. As such, when the plasma passes through the second semi-permeable membranes 8, the plasma can be in more adequate contact with the cells for substance metabolism. Compared with bioreactors in which the second semi-permeable membranes are vertically arranged, the cells are deposited in a larger area, which is advantageous for substance exchange.

Since the second semi-permeable membrane 8 near the outlet end of the connection pipe 23 is more prone to clogging, the design in which the pore diameters of the second semi-permeable membranes 8 are decreased one by one in the direction away from the outlet end of the connection pipe 23 enables the second semi-permeable membranes 8 not only to stabilize the plasma flow rate, but also to avoid clogging. Meanwhile, the pressure sensor 12 can detect whether there is a clogged second semi-permeable membrane 8. In the event of clogging, two backup outlets 11 are connected to prevent circulation interruption caused by the clogged second semi-permeable membrane 8 by allowing the plasma to pass through the backup connection pipe into the next second semi-permeable membrane 8 that is not clogged, so that the treatment can be continued.

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A bioartificial liver device comprising:
a housing comprising a top wall, a bottom wall, and a side wall;
a chamber confined by the housing;
a first semi-permeable membrane that is disposed within the chamber and subdivides the chamber into a plasma-separation chamber and a bioreaction chamber;
a plurality of hollow fiber filaments disposed in the plasma-separation chamber;
a blood inlet;
a blood cell outlet;
a first plasma opening;
a second plasma opening;
a separation pump;
a plurality of second semi-permeable membranes disposed in the bioreaction chamber;
a plurality of filter spaces;
a plurality of liver cell perfusion port;
a plasma outlet; and
a positive peristaltic pump;
wherein:
the top wall and the bottom wall are adapted to be disposed substantially horizontal with respect to the ground;
the top wall is adapted to be disposed above the bottom wall with respect to the ground;
the side wall connects the top wall with the bottom wall;
the blood inlet is disposed on the top wall and communicates with the plasma-separation chamber, for the purpose of introducing blood of a patient into the plasma-separation chamber;
the blood cell outlet is disposed on the bottom wall and communicates with the plasma-separation chamber;
one end of each hollow fiber filament communicates with the blood inlet, and the other end of the each hollow fiber filament communicates with the blood cell outlet;
the first plasma opening is disposed at the bottom of the side wall that is adjacent to the bottom wall and communicates with the plasma-separation chamber, for the purpose of outputting the plasma generated by the plasma-separation chamber from the plasma-separation chamber;
the second plasma opening is disposed on the bottom wall and communicates with the bioreaction chamber, for the purpose of introducing the plasma generated by the plasma-separation chamber into the bioreaction chamber;
the first and second plasma openings are connected with each other via the separation pump;
the second semi-permeable membranes are disposed substantially parallel to each other and to the top wall or the bottom wall;
each of the filter spaces is confined by two adjacent second semi-permeable membranes;
each of the liver cell perfusion ports is disposed on the side wall and communicates with one of the filter spaces, for the purpose of introducing liver cells into the filter spaces;
the plasma outlet is disposed on the top wall and communicates with the bioreaction chamber, for the purpose of outputting the plasma generated by the bioreaction chamber;
the blood cell outlet and the plasma outlet are connected to the positive peristaltic pump; and
the positive peristaltic pump is adapted to provide plasma generated by the bioartificial liver device into the body of the patient.

2. The device of claim 1, wherein the second semi-permeable membranes and the first semi-permeable membrane are flat membrane, and fixedly connected to the housing.

3. The device of claim 1, wherein pore diameters among the second semi-permeable membranes gradually decrease from the one of the second semi-permeable membranes that is adjacent to the bottom wall to the one of the second semi-permeable membranes that is adjacent to the top wall.

4. The device of claim 1, wherein a third semi-permeable membrane is provided in the plasma outlet to prevent cells, cell products, or macromolecular substances in the bioreaction chamber that trigger allergy from entering into the body of a patient.

5. The device of claim 1, wherein a gas space is confined by the bottom wall and the one of the second semi-permeable membranes that is disposed adjacent to the bottom wall; a gas inlet that introduces air having oxygen is disposed on the side wall and communicates with the gas space; and a plurality of fiber filaments each of the which breathes is disposed in the gas space and communicates with the gas inlet.

6. The device of claim 5, wherein a sealed stent plate is disposed in the gas space and between the gas inlet and the fiber filaments; the sealed stent plate is spaced from the gas inlet; the sealed stent plate comprises a plurality of orifices; one end of each fiber filament is clamped in one of the orifices.

7. The device of claim 1, wherein a plurality of pairs of a backup outlet and a pressure sensor is disposed on the side wall, each pair communicates with one filter space.

8. The device of claim 1, wherein a water inlet is provided in and communicates with the blood inlet.

9. The device of claim 1, wherein the side wall of the housing is provided with a gas outlet/reserved opening, and the gas outlet/reserved opening communicates with the gas space.

10. The device of claim 1, further comprising heat preservation jacket that functions to control the device at the temperature of 37° C., and a shaker that functions to shake the device; the heat preservation jacket covers the housing, and the shaker is arranged outside the housing and connected to the housing.

11. The device of claim 1, wherein a pore diameter on the first semi-permeable membrane is 0.3 to 5 micrometers, and a pore diameter on the one of the second semi-permeable membranes that is adjacent to the bottom wall is 5 micrometers.

12. The device of claim 1, wherein the first and second plasma openings are respectively connected to the separation pump via a connection pipe.

13. The device of claim 12, wherein a pressure detector is provided in the connection pipe.

* * * * *